(12) United States Patent
Salys

(10) Patent No.: US 7,558,632 B1
(45) Date of Patent: Jul. 7, 2009

(54) METHOD OF MANUFACTURING AN IMPLANTABLE J-SHAPED LEAD

(75) Inventor: Scott Salys, Plano, TX (US)

(73) Assignee: Pacesetter, Inc., Sylmar, CA (US)

( * ) Notice: Subject to any disclaimer, the term of this patent is extended or adjusted under 35 U.S.C. 154(b) by 494 days.

(21) Appl. No.: 11/459,315

(22) Filed: Jul. 21, 2006

Related U.S. Application Data

(62) Division of application No. 10/224,672, filed on Aug. 20, 2002, now abandoned.

(51) Int. Cl.
*A61N 1/05* (2006.01)
(52) U.S. Cl. .................................. 607/125; 607/122
(58) Field of Classification Search .................. 607/125
See application file for complete search history.

(56) References Cited

U.S. PATENT DOCUMENTS

| | | | |
|---|---|---|---|
| 4,394,866 A | 7/1983 | Hughes | |
| 4,402,328 A * | 9/1983 | Doring | 607/125 |
| 4,402,330 A | 9/1983 | Lindemans | |
| 4,454,888 A | 6/1984 | Gold | |
| 4,488,561 A | 12/1984 | Doring | |
| 5,387,233 A | 2/1995 | Alferness et al. | |
| 5,483,022 A | 1/1996 | Mar | |
| 5,628,779 A | 5/1997 | Bornzin et al. | |
| 5,772,693 A | 6/1998 | Brownlee | |
| 6,321,123 B1 | 11/2001 | Morris et al. | |
| 2002/0049485 A1 | 4/2002 | Smits | |

* cited by examiner

*Primary Examiner*—Kennedy J Schaetzle

(57) ABSTRACT

An implantable multi-conductor endocardial lead for a cardiac stimulator includes a tubular lead body of flexible resilient insulative material having a first lumen and a smaller diameter tubular member of similar material having a second lumen is coaxially received in the first lumen. An outer coil conductor is received within an annular cavity between the tubular lead body and the tubular member. An elongated inner coil conductor is received within the second lumen. A tip electrode at the distal end of the lead is coupled to the inner coil conductor and a ring electrode proximally spaced from the tip electrode is coupled to the outer coil conductor. All components except for the outer coil conductor have a normally straight configuration and the outer coil conductor is pre-shaped into a generally circular looped configuration such that, upon assembly, the resulting endocardial lead results in a J-configuration at its distal end.

18 Claims, 4 Drawing Sheets

METHOD OF MANUFACTURING AN IMPLANTABLE J-SHAPED LEAD

CROSS-REFERENCE TO RELATED APPLICATION

This application is a divisional of U.S. patent application Ser. No. 10/224,672, filed Aug. 20, 2002, titled "IMPLANTABLE J-SHAPED LEAD," now abandoned.

FIELD OF THE INVENTION

The present invention relates generally to lead assemblies for implantable medical devices which provide stimulating pulses to selected body tissue, and more particularly, to a unique configuration of such lead assemblies.

BACKGROUND OF THE INVENTION

Although it will become evident to those skilled in the art that the present invention is applicable to a variety of implantable medical devices utilizing pulse generators to stimulate selected body tissue, the invention and its background will be described principally in the context of a specific example of such devices, namely, cardiac pacemakers for providing precisely controlled stimulation pulses to the heart. However, the appended claims are not intended to be limited to any specific example or embodiment described herein.

Pacemaker leads form the electrical connection between the cardiac pacemaker pulse generator and the heart tissue which is to be stimulated. As is well known, the leads connecting such pacemakers with the heart may be used for pacing, or for sensing electrical signals produced by the heart, or for both pacing and sensing in which case a single lead serves as a bi-directional pulse transmission link between the pacemaker and the heart. An endocardial type lead, that is, a lead which is inserted into a vein and guided therethrough into a cavity of the heart, includes at its distal end an electrode designed to contact the endocardium, the tissue lining the inside of the heart. The lead further includes a proximal end having a connector pin adapted to be received by a mating socket in the pacemaker. A flexible, coil conductor surrounded by an insulating tube or sheath typically couples the connector pin at the proximal end and the electrode at the distal end.

The implantable cardiac stimulator with which the present lead invention is concerned may take the form of a pacemaker capable of pacing and sensing in at least one chamber of the heart. Indeed, the present invention, may relate to a programmable dual chamber pacemaker wherein the basic configuration of the pacemaker, e.g. unipolar or bipolar, can be changed, including the grounding configuration and ground potentials used within the pacemaker.

Generally, a heart stimulator, commonly known as a "pacemaker" or "pacer", uses one or two flexible leads having one end connected to the pacer and the other end connected to electrodes placed in close proximity to the heart. These leads are used to stimulate or pace the heart. Also, these leads are used to sense the heart activity by picking up electrical signals from the heart.

In order to properly pace or sense, the pacer has to be able to deliver a stimulating pulse to the heart or sense an electrical signal from the heart, and this requires that there be an electrical return path. If, within a given heart chamber, a unipolar lead is used—containing a single conductor—the return path is the conductive body tissue and fluids. The return path is connected to the pacer by connecting the pacer electrical common or ground to the pacer metal enclosure, typically referred to as the pacer case or housing. The case, in turn, makes contact with the body tissue and/or fluids.

An alternative solution to using a unipolar lead in a given heart chamber is to use a double lead/electrode in the heart chamber, known as a bipolar lead. In a bipolar lead, a second conductor is spiraled over and insulated from a first conductor along the length of the lead. At the distal end of the lead, one of the conductors is connected to a first electrode, referred to as the "tip" electrode, and the second conductor is connected to a second electrode, referred to as a "ring" electrode. The ring electrode is generally situated about 8 to 20 mm from the tip electrode. The tip electrode is typically placed in contact with heart tissue, while the ring electrode is in electrical contact with the blood. Because both body tissue and fluids are conductive, the ring electrode of a bipolar lead, in contact with the body fluids, serves as an electrical return for both pacing and sensing.

As indicated, pacing or sensing using the pacer case or enclosure as part of the electrical return path is known as unipolar pacing or sensing. Pacing or sensing using the lead ring electrode and associated lead conductor as the electrical return path is known as bipolar pacing or sensing. There are numerous factors to consider when deciding whether unipolar or bipolar pacing and/or sensing should be used. Bipolar pacing has, in general, the advantage of requiring less energy than unipolar pacing. Further, bipolar sensing is less prone to crosstalk and myopotential sensing than is unipolar sensing. Crosstalk generally refers to a pacer mistakenly sensing a heart activity in one heart chamber immediately after the other chamber is paced. Bipolar sensing reduces crosstalk resulting from a pacing stimulus in the opposite chamber. Bipolar pacing is preferred if pectoral or diaphragmatic stimulation occurs.

Unipolar pacing and sensing offers the advantage, in general, of simpler circuitry within the pacemaker and a smaller diameter lead. Some physicians prefer unipolar over bipolar pacing and/or sensing as a function of other implantation and heart conditions. Depending on the lead orientation, unipolar sensing may be preferable to bipolar sensing.

Cardiac rhythm management (CRM) is a growing yet maturing industry in which product design is becoming less differentiated. As this industry matures and profit margins tighten, increasing importance lies in making quality products that are low cost and easily produced. A commonly produced product in CRM is a "J" configured lead that delivers electrical pulses from the generator to the atrium of the heart. This "J" lead achieves its "J" shape through the use of pre-shaped components. A new design that reduces the number of pre-shaped components and improves manufacturing ease is needed to lower costs and improve manufacturability.

A new "J" lead design that is low cost and more easily produced is accomplished by reducing the number of pre-shaped components. The new design of the invention uses fewer pre-shaped components, thereby improving manufacturability and lowering cost.

The common industry "J" lead design employs a "J" formed outer tube and a "J" formed outer coil conductor. The thin and flexible inner coil conductor and inner tube are both in a straight configuration. To form each "J" shaped component adds cost, and in the case of silicone tubing can more than double the price. Separate from component cost, multiple pre-formed "J" components require alignment of each during the manufacturing process. If the "J" formed outer tubing and coil conductor are not aligned properly, the assembled lead will not have the correct "J" configuration.

The "J" lead design of the invention uses a single preshaped looped outer coil conductor with a straight inner coil conductor, inner tube, and outer tube. The use of these components results in a final "J" lead that is generally similar to the final "J" lead, but with cost and manufacturability advantages. The straight outer tubing of the looped coil conductor design is significantly less expensive than the "J" formed tube used in a conventional design. In addition to the cost advantage gained in these high volume products, a single looped coil conductor design allows for a more easily assembled product.

This looped coil conductor "J" lead design thus gives the assignee of this technology a production and cost advantage at a time when producing quality lead products cheaper and faster is of ever increasing importance.

A couple of patents are considered to be generally illustrative of the prior art. U.S. Pat. No. 4,488,561 to Doring discloses a body implantable lead which may be easily provided with a desired predetermined curve or bend. As such, the disclosed invention allows for a pacing lead convertible from use in the ventricle to use in the atrium or other desired location. A stylet wire having a generally straight configuration is removably mounted within a concentric memory coil conductor tending to assume the desired curved shape. The stylet and memory coil conductor may be inserted together within the lead body, the stylet maintaining the memory coil conductor in a generally straight configuration. After removal of the stylet, the memory coil conductor urges the lead body to assume the desired predetermined curve, facilitating use of the lead in the atrium.

U.S. Patent Application Publication No. US 2002/0049485 published on Apr. 25, 2002 discloses an elongated coronary vein lead having a variable stiffness lead body most preferably adapted to be advanced into a selected coronary vein for delivering a pacing or defibrillation signal to a predetermined region of a patient's heart, such as the left ventricle. The variable stiffness lead body enhances the ability of the lead to be retained in a coronary vein after the lead has been implanted.

It was in light of the foregoing that the present invention was conceived and has now been reduced to practice.

SUMMARY

The invention, then, concerns an implantable multi-conductor endocardial lead for a cardiac stimulator which includes a tubular lead body of flexible resilient insulative material having a first lumen and a smaller diameter tubular member of similar material having a second lumen is coaxially received in the first lumen. An outer coil conductor is received within an annular cavity between the tubular lead body and the tubular member. An elongated inner coil conductor is received within the second lumen. A tip electrode at the distal end of the lead is coupled to the inner coil conductor and a ring electrode proximally spaced from the tip electrode is coupled to the outer coil conductor. All components except for the outer coil conductor have a normally straight configuration and the outer coil conductor is pre-shaped into a generally circular looped configuration such that, upon assembly, the resulting endocardial lead results in a "J"-configuration at its distal end.

A primary feature, then, of the present invention is the provision of a lead assembly connecting an implantable medical device with the tissue to be stimulated exhibiting a unique configuration.

Another feature of the present invention is the provision of such a unique lead assembly which exhibits improved handling characteristics during implantation.

Yet another feature of the present invention is the provision of such a unique lead assembly which minimizes cost and is more easily produced by reducing the number of pre-shaped components.

Still another feature of the present invention is the provision of such a unique lead assembly in which a single preformed looped outer coil conductor is used to create a "J" lead configuration, all other lead body components being of a straight configuration when in the free state.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein.

DETAILED DESCRIPTION OF THE PREFERRED EMBODIMENT

Figure 1:
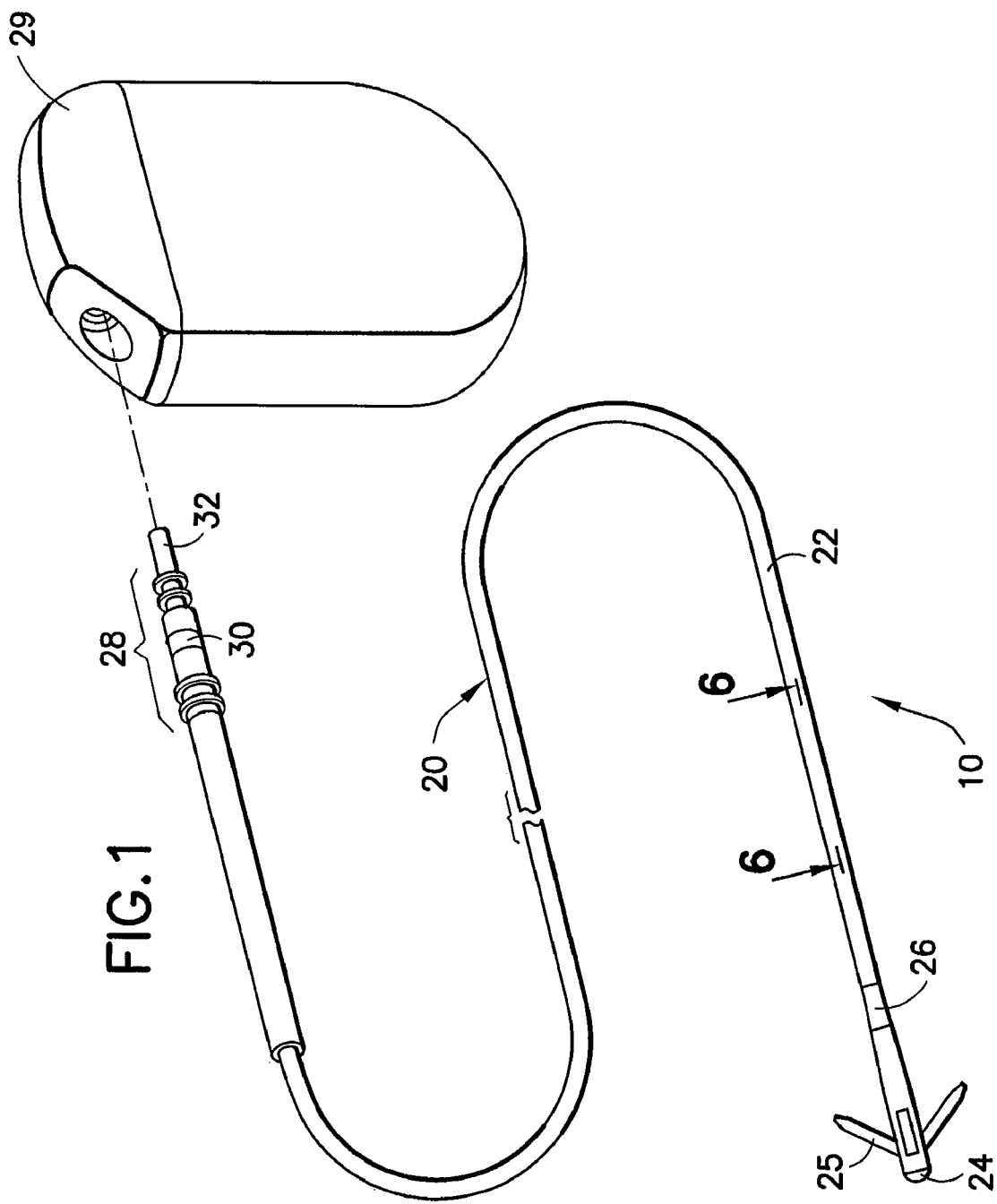
FIG. 1 is a perspective exploded view of a body implantable lead positioned for engagement at one end with heart tissue, for example, and at the other end for insertion into a body stimulation device such as a pacemaker.

Refer now to the drawings and, initially, to FIG. 1 in which is shown a diagrammatic perspective view of an implantable system 10 for providing electrical stimulation of a heart, for example, incorporating features of the present invention. Although the present invention will be described with reference to the embodiments shown in the drawings, it should be understood that the present invention can be embodied in many alternate forms or embodiments. In addition, any suitable size, shape or type of elements or materials could be used.

The lead 20, illustrated to be of a multi-conductor endocardial bipolar design, includes an insulating sheath 22 interconnecting a distal tip electrode 24 secured adjacent an interior wall of an organ such as the heart by means, for example, of fixing tines 25 which engage the tissue or trabeculae of the heart and an electrical connector 28 at a proximal end to which can be attached a source of electrical energy such as a pacemaker 29. In a known manner, connector ring terminal 30 of the electrical connector 28 is electrically in common with an anode ring electrode 26 at the distal end of the lead 20, and connector pin terminal 32 is electrically in common with the cathode tip electrode 24 at the distal end of the lead.

Figure 2:
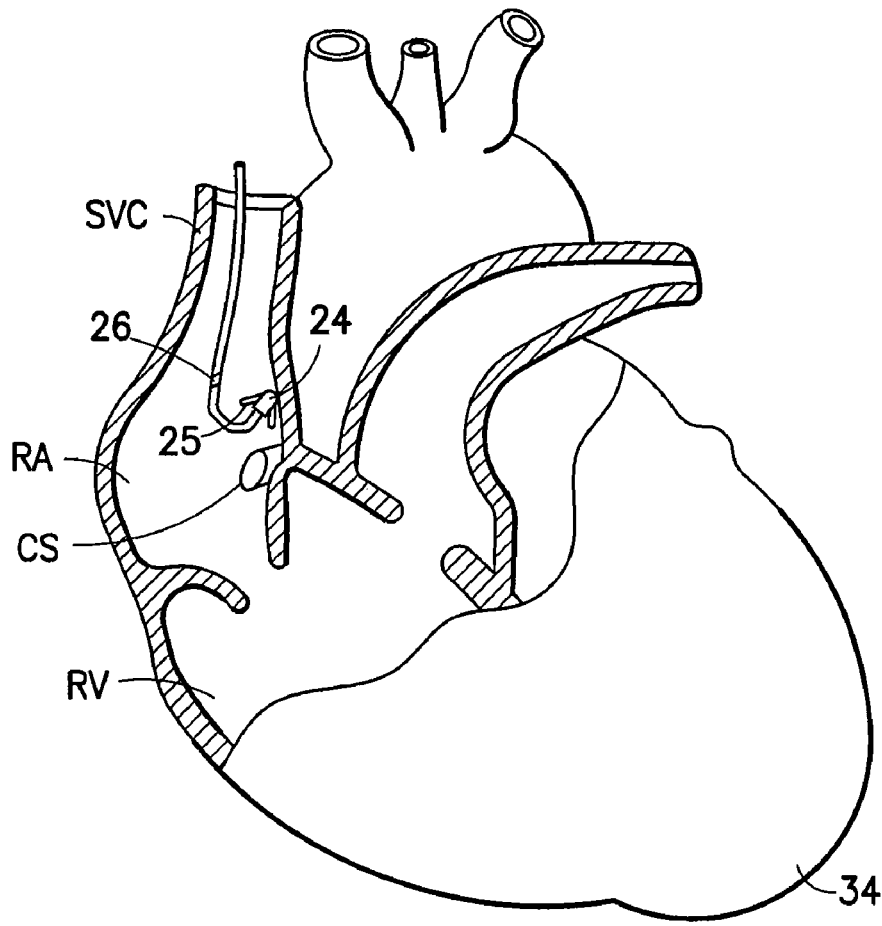
FIG. 2 is a diagrammatic perspective view illustrating the distal end of an implanted lead system embodying the present invention for providing electrical stimulation of a heart.

Turn now briefly to FIG. 2 which illustrates a human heart 34, partially cut away and in section, showing the right atrium RA and the right ventricle RV along with the coronary sinus CS. The lead 20 is shown in a typical placement, being an RA lead. The lead 20 extends to the distal tip electrode 24 shown in the appendage of the right atrium RA and illustrates a typical position of the lead in the appendage of the right atrium and a typical "J" configuration of the lead at this location.

It was earlier explained that a "J" configured lead, such as the lead 20 that delivers electrical pulses from the pulse generator, or pacemaker, 29 to the atrium RA of the heart 34 achieves its "J" shape through the use of pre-shaped components and that the focus of the present invention is to reduce the number of pre-shaped components and improve manufacturing ease to lower costs and improve manufacturability.

Figure 3:
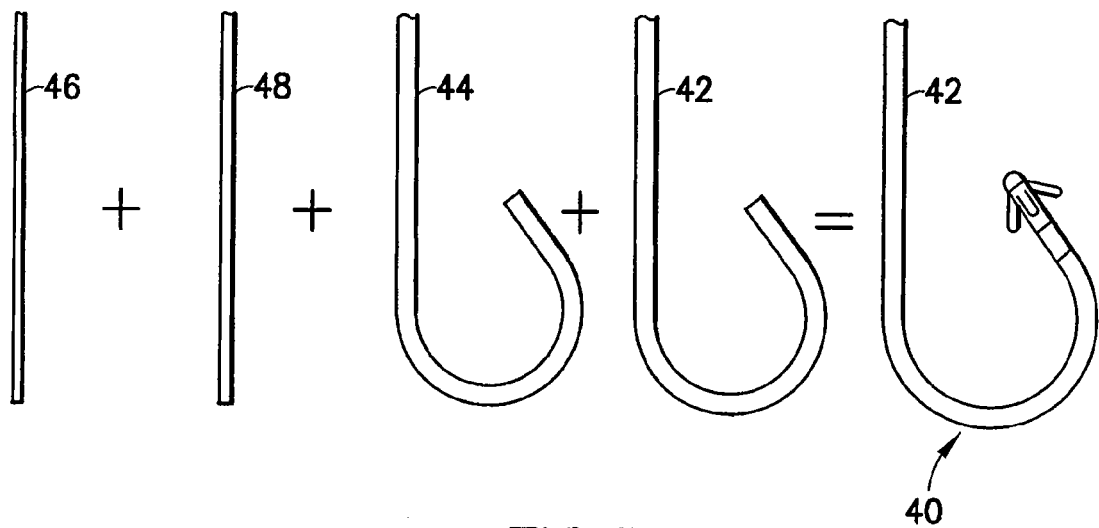
FIG. 3 is a diagrammatic elevation view illustrating a combination of components comprising a known lead system.
Figure 4:
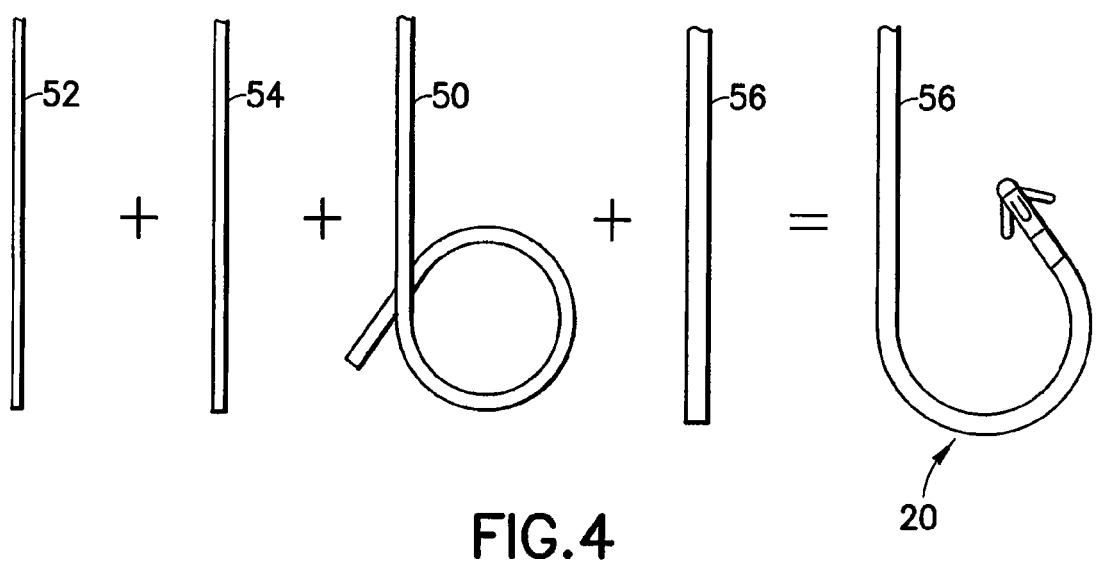
FIG. 4 is a diagrammatic elevation view illustrating a combination of components comprising the lead system of the invention.

A new "J" lead design that is low cost and more easily produced is accomplished by reducing the number of pre-shaped components. In this regard, FIG. 3 illustrates a typical current common industry configuration used to achieve a "J" shaped lead 40 while FIG. 4 illustrates the lead 20 of the invention that uses fewer pre-shaped components, thus improving manufacturability and lowering cost. However, before describing the new lead of the invention, it is well to describe the current common industry design which is to be improved upon. Thus, the known "J" lead design 40 of FIG. 3 includes a "J" formed outer tube 42 which is particularly expensive to fabricate and a "J" formed outer coil conductor 44. An inner coil conductor 46 and inner tube 48, both of which are thin and flexible, are also both of a straight configuration. As noted, to form each "J" shaped component adds cost, and in the case of silicone tubing, which is a preferred material for the outer tube 42 (as well as the inner tube 48 which is straight in configuration) can be more than double the price of a straight component. The added cost associated with "J" formed tubing is the result of increased processing and handling time required for forming straight extruded tubing as well as cutting the shaped tubing to the appropriate length. Tubing is inherently manufactured in a straight configuration and cut using automated processes making straight tubing significantly less expensive. In addition to the component cost, multiple pre-formed "J" components require mutual alignment during the manufacturing and assembly process. If the "J" formed outer tube 42 and outer coil conductor 44 are not aligned properly, the assembled lead 40 will not result in having the correct "J" configuration.

The new "J" lead 20 of the invention as illustrated in FIG. 4 uses a single pre-shaped looped outer coil conductor 50 with a straight inner coil conductor 52, straight inner tube 54 of flexible polymeric insulating material, and straight outer tube 56 also of flexible polymeric insulating material. The outer tube 56 is the same component as the insulating sheath 22 but here re-numbered for consistency with the other described components in FIG. 4. The use of these components results in a final "J" lead that is equivalent to the final "J" lead of FIG. 3, but with considerable cost and manufacturability advantages. The straight outer tubing of the looped coil conductor design is significantly less expensive than the "J" formed tube used in conventional lead configurations. In addition to the cost advantage gained in these high volume products, a single looped coil conductor design allows for a more easily assembled product. This looped coil conductor "J" lead design thus gives the owner of this technology a production and cost advantage at a time when producing quality lead products cheaper and faster is of ever increasing importance.

Figure 5:
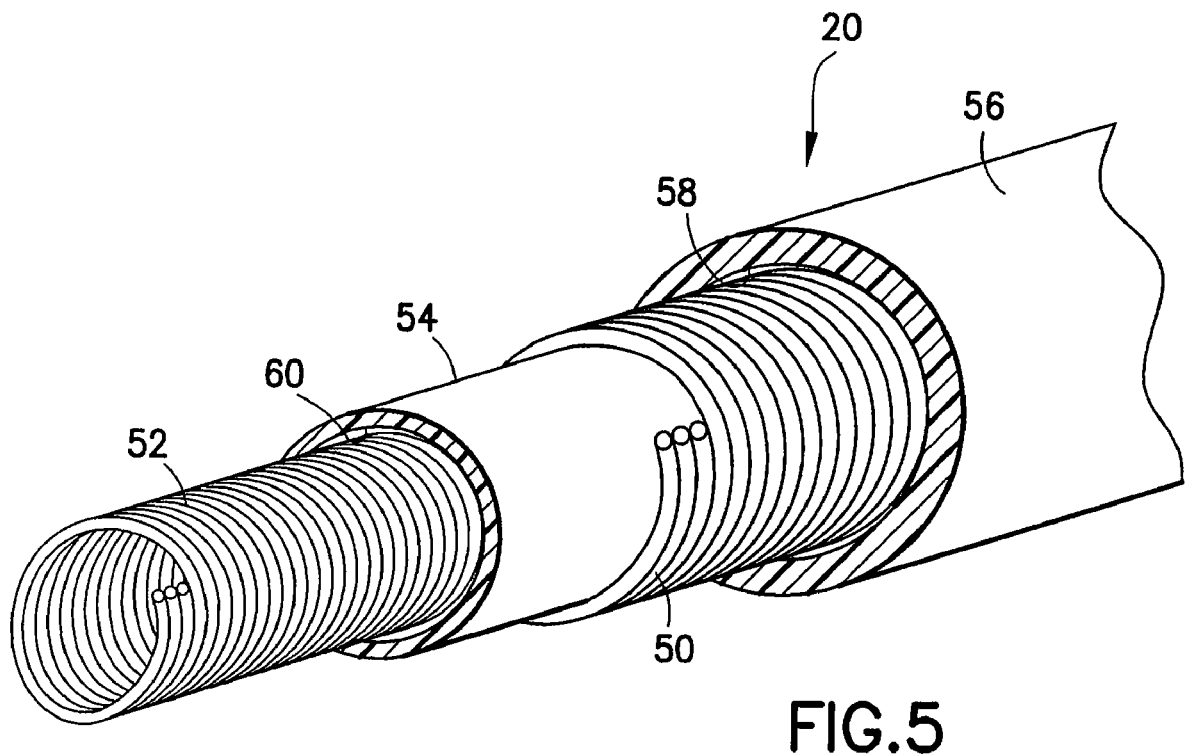
FIG. 5 is a perspective view, certain portions being cut away and shown in section, illustrating in greater detail the lead system illustrated in FIGS. 1, 2, and 4.
Figure 6:
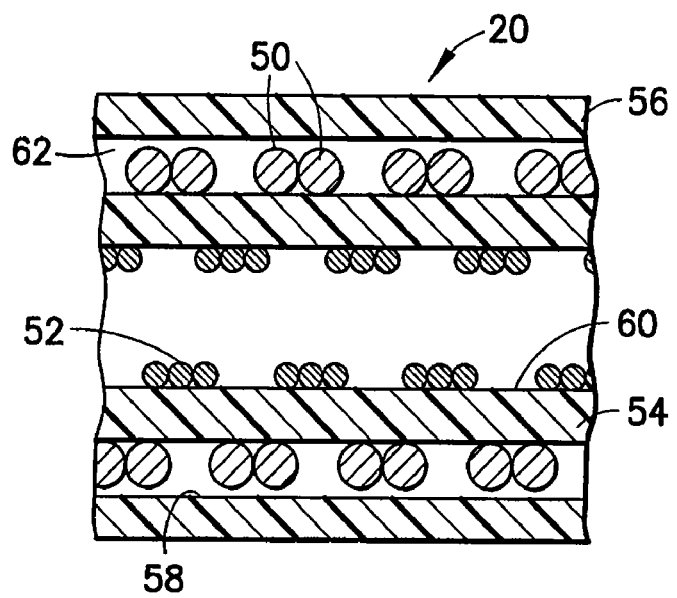
FIG. 6 is a cross section view taken generally along line 6-6 in FIG. 1.

Turn now, particularly, to FIGS. 5 and 6 for a more detailed description of the invention. The lead 20 includes an elongated tubular lead body 56, or outer tube, of flexible resilient insulative material having a first longitudinally extending lumen 58. An elongated tubular member 54, or inner tube, also of flexible resilient insulative material, has a second longitudinally extending lumen 60 received in and coaxial with the first longitudinally extending lumen 58, the tubular member having an outer diameter smaller than the inner diameter of the first lumen thereby defining an annular cavity 62.

The outer coil conductor 50 is fashioned into the circular looped configuration illustrated in FIG. 4 in a known manner either by being mechanically stressed or by being thermally stressed, then is suitably received within the annular cavity 62 between the tubular lead body 56 and the tubular member 54, extending between the proximal and distal ends of the lead. The inner coil conductor 52 is similarly suitably received within the second longitudinally extending lumen 60 and also extends between the proximal and distal ends of the lead 20.

As earlier mentioned, the tip electrode 24 at the distal end of the lead is coupled to the inner coil conductor 52 and the ring electrode 26 on the lead 20 is proximally spaced from the tip electrode and is coupled to the outer coil conductor 50. Also, as earlier mentioned, the tubular lead body 56, the tubular member 54, and the inner coil conductor 52 all have a normally straight configuration when in the free state while the outer coil conductor 50 is pre-shaped into a generally circular looped configuration.

Upon assembly of the lead body 56, the tubular member 54, the outer coil conductor 50, and the inner coil conductor 52, the resulting endocardial lead 20 is caused to result in a "J"-configuration at its distal end.

Figure 7:
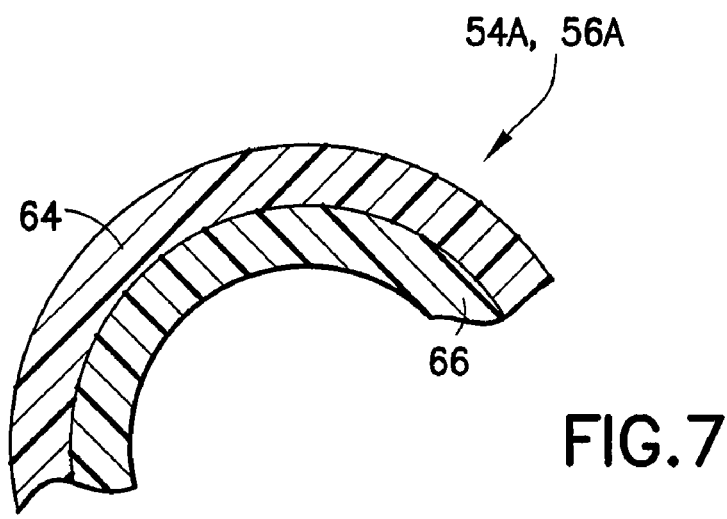
FIG. 7 is a detail cross section view illustrating another embodiment of a component of the invention.

For purposes of the invention, the lead body 56 and the tubular member 54 may variously be composed of silicone rubber, or of polyurethane, or of a chemical composite of silicone rubber and polyurethane, or of a layered composite of silicone rubber and polyurethane. This last configuration is represented in FIG. 7 by a modified lead body 56A or tubular member 54A, each or either of which is constructed of a layer 66 of silicone rubber and a layer 64 of polyurethane, the layers being bonded or interference fit together by any suitable technique.

In an alternate embodiment, the tubular member 54 and inner coil conductor 52 are integrally formed, with the tubular member 54 being in the form of an insulative layer on the outer surface of inner coil conductor 52, thereby insulating inner coil conductor 52 from outer coil conductor 50.

It should be understood that the foregoing description is only broadly illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A method of fabricating an implantable multi-conductor endocardial lead extending between proximal and distal ends for use with a cardiac stimulation device, the endocardial lead including a tip electrode at the distal end and a ring electrode proximally spaced from the tip electrode, the method comprising:

(a) providing an elongated tubular lead body of flexible resilient insulative material having a first longitudinally extending lumen with an inner diameter;

(b) inserting coaxially into the first longitudinally extending lumen an elongated tubular member of flexible resilient insulative material having a second longitudinally extending lumen, the tubular member having an outer diameter smaller than the inner diameter of the first lumen thereby defining an annular cavity;

(c) inserting into the annular cavity between the tubular lead body and the tubular member an outer coil conductor extending between the proximal and distal ends thereof;

(d) inserting into the second longitudinally extending lumen an inner coil conductor extending between the proximal and distal ends thereof;

(e) coupling the tip electrode to the inner coil conductor;

(f) coupling the ring electrode to the outer coil conductor;

(g) pre-shaping the outer coil conductor into a generally circular looped configuration while maintaining a normally straight configuration for the tubular lead body, the tubular member, and the inner coil conductor when in a free state; and (h) assembling the lead body, tubular member, outer coil conductor, and inner coil conductor such that the resulting endocardial lead is caused to result in a J-configuration at its distal end.

2. A method of fabricating an implantable multi-conductor endocardial lead as set forth in claim 1:
   wherein the lead body and the tubular member are composed of silicone rubber.

3. A method of fabricating an implantable multi-conductor endocardial lead as set forth in claim 1:
   wherein the lead body and the tubular member are composed of polyurethane.

4. A method of fabricating an implantable multi-conductor endocardial lead as set forth in claim 1:
   wherein the lead body and the tubular member are composed of a chemical composite of silicone rubber and polyurethane.

5. A method of fabricating an implantable multi-conductor endocardial lead as set forth in claim 1:
   wherein the lead body and the tubular member are composed of a layered composite of silicone rubber and polyurethane.

6. A method of fabricating an implantable multi-conductor endocardial lead as set forth in claim 1:
   wherein the lead body and the tubular member are composed of a flexible polymeric insulating material.

7. A method of fabricating an implantable multi-conductor endocardial lead as set forth in claim 1 further comprising:
   (i) individually coupling an electrical connector to the proximal ends, respectively, of the outer coil conductor and of the inner coil conductor.

8. A method of fabricating an implantable multi-conductor endocardial lead extending between proximal and distal ends for use with a cardiac stimulation device, the endocardial lead having a tip electrode at the distal end and a ring electrode proximally spaced from the tip electrode, the method comprising:
   (a) providing an elongated, discrete first tube of flexible resilient insulative material having a first longitudinal extending lumen with an inner diameter;
   (b) inserting coaxially into the first longitudinally extending lumen an elongated, discrete second tube of flexible resilient insulative material having a second longitudinally extending lumen, the second tube having an outer diameter smaller than the inner diameter of the first lumen thereby defining an annular cavity;
   (c) inserting into the annular cavity between the first tube and the second tube an outer helical coil conductor extending between the proximal and distal ends thereof;
   (d) inserting into the second longitudinally extending lumen an inner helical coil conductor extending between the proximal and distal ends thereof;
   (e) coupling the tip electrode to the inner helical coil conductor;
   (f) coupling the ring electrode to the outer helical coil conductor;
   (g) pre-shaping the outer helical coil conductor into a generally circular looped configuration while maintaining a normally straight configuration for the first tube, the second tube, and the inner helical coil conductor when in a free state; and
   (h) assembling the first tube, the second tube, outer helical coil conductor, and inner helical coil conductor such that the resulting endocardial lead is caused to result in a J-configuration at its distal end.

9. A method of fabricating an implantable multi-conductor endocardial lead as set forth in claim 8:
   wherein the first tube is a lead body and the second tube is a tubular member; and
   wherein the lead body and the tubular member are composed of silicone rubber.

10. A method of fabricating an implantable multi-conductor endocardial lead as set forth in claim 8:
    wherein the first tube is a lead body and the second tube is a tubular member; and
    wherein the lead body and the tubular member are composed of polyurethane.

11. A method of fabricating an implantable multi-conductor endocardial lead as set forth in claim 8:
    wherein the first tube is a lead body and the second tube is a tubular member; and
    wherein the lead body and the tubular member are composed of a chemical composite of silicone rubber and polyurethane.

12. A method of fabricating an implantable multi-conductor endocardial lead as set forth in claim 8;
    wherein the outer helical coil conductor is generally circularly looped to bias the first tube, the second tube, and the inner helical coil conductor to a generally J-shaped configuration.

13. A method of fabricating an implantable multi-conductor endocardial lead extending between proximal and distal ends for use with a cardiac stimulation device, the method comprising:
    (a) providing a first tube of flexible resilient insulative material having a first longitudinal extending lumen with an inner diameter;
    (b) inserting coaxially into the first longitudinally extending lumen a second tube of flexible resilient insulative material having a second longitudinally extending lumen, the second tube having an outer diameter smaller than the inner diameter of the first lumen thereby defining an annular cavity;
    (c) inserting into the annular cavity between the first tube and the second tube an outer coil conductor extending between the proximal and distal ends thereof;
    (d) inserting into the second longitudinally extending lumen an inner coil conductor extending between the proximal and distal ends thereof;
    (e) pre-shaping the outer coil conductor into a generally circular looped configuration while maintaining a normally straight configuration for the first tube, the second tube, and the inner coil conductor when in a free state; and (f) assembling the first tube, the second tube, outer coil conductor, and inner coil conductor such that the resulting endocardial lead is caused to result in a J-configuration at its distal end.

14. A method of fabricating an implantable multi-conductor endocardial lead as set forth in claim 13:

wherein the first tube is a lead body and the second tube is a tubular member; and wherein the lead body and the tubular member are composed of silicone rubber.

15. A method of fabricating an implantable multi-conductor endocardial lead as set forth in claim 13:

wherein the first tube is a lead body and the second tube is a tubular member; and wherein the lead body and the tubular member are composed of polyurethane.

16. A method of fabricating an implantable multi-conductor endocardial lead as set forth in claim 13:

wherein the first tube is a lead body and the second tube is a tubular member; and wherein the lead body and the tubular member are composed of a chemical composite of silicone rubber and polyurethane.

17. A method of fabricating an implantable multi-conductor endocardial lead as set forth in claim 13;

wherein the outer coil conductor is generally circularly looped to bias the first tube, the second tube, and the inner coil conductor to a generally J-shaped configuration.

18. A method of fabricating an implantable multi-conductor endocardial lead as set forth in claim 13 further comprising:

(g) coupling a tip electrode to the inner coil conductor, the tip electrode disposed at the distal end of the first tube; and (h) coupling a ring electrode to the outer coil conductor, the ring electrode being proximally spaced from the tip electrode.

* * * * *